United States Patent [19]

Strohmaier

[11] Patent Number: 4,534,732

[45] Date of Patent: Aug. 13, 1985

[54] DENTAL HANDPIECE

[75] Inventor: Ernst Strohmaier, Bd. Schussenried, Fed. Rep. of Germany

[73] Assignee: Kaltenbach & Voigt GmbH & Co., Fed. Rep. of Germany

[21] Appl. No.: 592,693

[22] Filed: Mar. 23, 1984

[30] Foreign Application Priority Data

Sep. 9, 1983 [DE] Fed. Rep. of Germany ....... 3332627

[51] Int. Cl.$^3$ ............................................. A61C 3/00
[52] U.S. Cl. ..................................... 433/29; 433/126
[58] Field of Search ................................ 433/29, 126

[56] References Cited

U.S. PATENT DOCUMENTS

| | | | |
|---|---|---|---|
| 2,038,911 | 4/1936 | Stutz et al. ............................... | 433/29 |
| 4,260,382 | 4/1981 | Thomson ............................... | 433/29 |
| 4,330,274 | 5/1982 | Friedman et al. ..................... | 433/29 |
| 4,403,956 | 9/1983 | Nakanishi ............................... | 433/29 |
| 4,403,959 | 9/1983 | Hatakeyama ......................... | 433/126 |
| 4,460,337 | 7/1984 | Landgraf et al. ..................... | 433/29 |

FOREIGN PATENT DOCUMENTS 1412622 11/1975 United Kingdom ................. 433/29

Primary Examiner—John J. Wilson
Attorney, Agent, or Firm—Scully, Scott, Murphy and Presser

[57] ABSTRACT

A dental handpiece, consisting of a connector portion and an elongated, exchangeable gripping sleeve portion which is coupled to the connector portion so as to be rotatable about its axis, and which includes a treating implement arranged at the sleeve end distant from the connector portion. An incandescent lamp or lightbulb is eccentrically arranged within the handpiece, and a light conductor is located in the gripping sleeve portion and has its end remote from the connector portion directed towards the area of the implement, and whose end which is distant from the implement is suppliable with light from the incandescent lamp.

21 Claims, 7 Drawing Figures

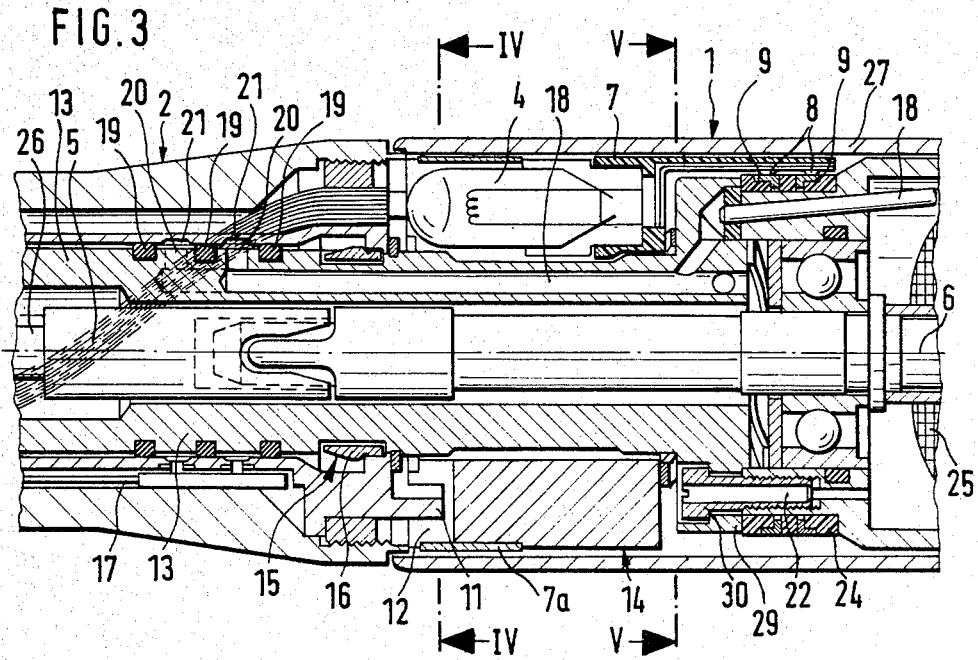
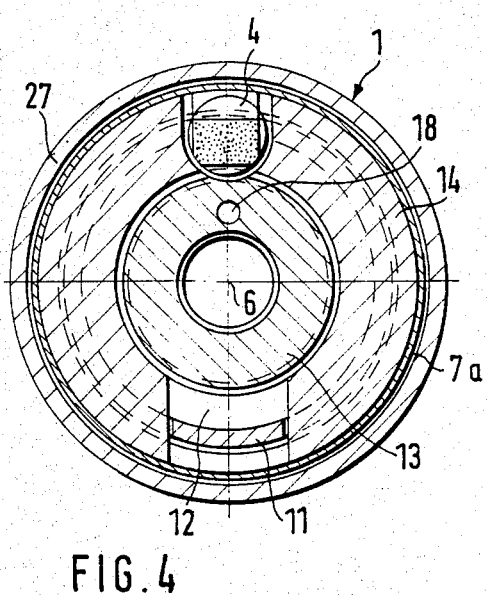
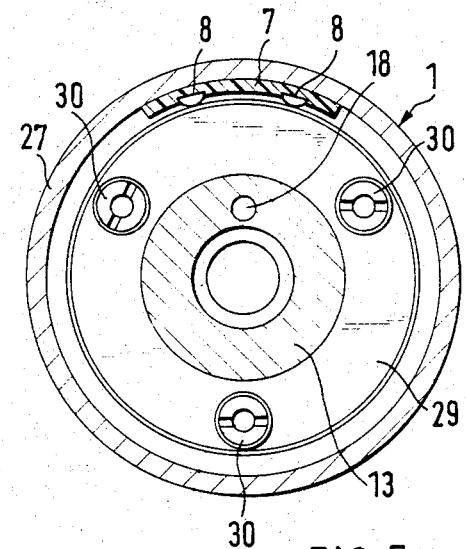

DENTAL HANDPIECE

BACKGROUND OF THE INVENTION

1. Field of the Invention

The present invention relates to a dental handpiece, consisting of a connector portion and an elongated, exchangeable gripping sleeve portion which is coupled to the connector portion so as to be rotatable about its axis, and which includes a treating implement arranged at the sleeve end distant from the connector portion. An incandescent lamp or lightbulb is eccentrically arranged within the handpiece, and a light conductor is located in the gripping sleeve portion and has its end remote from the connector portion directed towards the area of the implement, and whose end which is distant from the implement is suppliable with light from the incandescent lamp.

2. Discussion of the Prior Art

A handpiece of that type, in which the gripping sleeve portion and the connector portion are rotatable relative to each other, has become known from the disclosure of German Laid-open Patent Application No. 31 32 995. The surface at the end of the connector portion facing towards the gripping sleeve portion incorporates a light-transmitting ring for effecting light transmission to the light conductor which is located in the gripping sleeve portion, and wherein the ring is either directly supplied with light from the incandescent lamp or indirectly through an intermediate light conductor which is supplied with light from the incandescent lamp. The end of the light conductor in the gripping sleeve portion facing towards the connector portion is formed as a light-receiver ring. The arrangement of light rings of that type, among other circumstances, produces light losses due to the unavoidable light dispersion, as a result of which, there is encountered an inadequate illumination of the location on the tooth which is to be treated.

SUMMARY OF THE INVENTION

Accordingly, it is an object of the present invention, as can be clearly ascertained from the description thereof as set forth hereinbelow, to eliminate the disadvantages encountered in the prior art, in that a handpiece of the above-mentioned constructional type incorporating handpiece portions which are rotatable relative to each other, facilitates the direct light transmission from the incandescent lamp or lightbulb to the end of light conductor in the gripping sleeve component facing towards the connector portion.

The advantages which are achieved through intermediary of the present invention can be essentially ascertained in that, as a result of the common rotatability of the incandescent lamp and gripping sleeve portion, the end of the light conductor in the gripping sleeve portion facing towards the connector is, in every rotational position thereof, directly supplied with light from the incandescent lamp, so as to thereby avoid light losses such as are encountered in known instance due to the interposition of a lightring.

BRIEF DESCRIPTION OF THE DRAWINGS

Reference may now be had to the following detailed description of preferred embodiments of the invention, taken in conjunction with the accompanying drawings; in which:

FIG. 3 illustrates, on an enlarged scale, a sectional view of the encircled portion III in FIG. 1;

FIG. 4 illustrates a sectional view taken along line IV—IV in FIG. 3;

FIG. 5 illustrates a sectional view taken along line V—V in FIG. 3;

DETAILED DESCRIPTION

Figure 1:
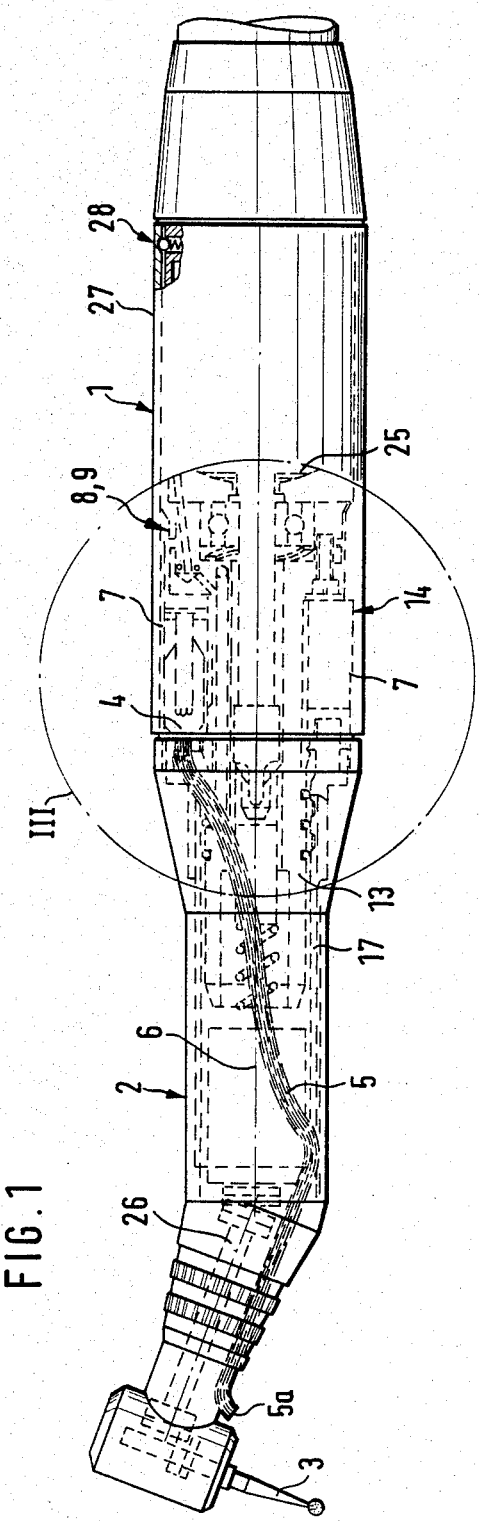
FIG. 1 illustrates a side view of a dental handpiece pursuant to the invention.

The dental handpiece consists of a connector portion 1 and an elongated, interchangeable gripping sleeve portion 2 which can be coupled to the connector portion 1 so as to be axially rotatable, and with the sleeve incorporating a treating implement 3 located at the sleeve end distant from the connector portion. An incandescent lamp or lightbulb 4 is arranged eccentrically interiorly of the handpiece in proximity to the outer wall structure thereof. A light conductor 5 is arranged interiorly of the gripping sleeve portion 2, having the end 5a thereof distant from the connector portion directed towards the area of the treating implement, with the light conductor end remote from the implement being suppliable with light from the incandescent lamp 4.

The incandescent lamp or lightbulb 4 is arranged so as to be rotatable, in conjunction with the gripping sleeve portion 2, relative to the connector portion 1, and is connected through the intermediary of slide contacts 8, as well as through contact rings 9, with power current supply lines 10 which are arranged in the connector portion 1.

Basically, it is possible to provide for the arrangement of the incandescent lamp 4 in the gripping sleeve portion 2. Thus, the incandescent lamp or lightbulb 4 can be arranged on a support 7 rotatable in a circular path about the longitudinal axis 6 of the handpiece. In the drawing there is, accordingly, represented the arrangement of the incandescent lamp 4 in the connector portion 1, and, in effect, in the manner wherein the retainer or support 7 which receives the incandescent lamp 4 is located at the end of the connector portion 1 towards the gripping sleeve portion and, for transmission of the rotational movement of the gripping sleeve portion 2, is provided with engaging means 12 which engage with cooperating engaging means 11 on the gripping sleeve portion 2 upon alignment of the incandescent lamp and the light conductor end which is distant from the implement.

The incandescent lamp is readily exchangeable; for example, upon the handpiece 1, 2 being separated, can be withdrawn in an axial direction towards the left from the retainer 7 and, as a result, from the connector portion 1. There can also be provided a version in which the retainer 7 is arranged so as to be exchangeable for the incandescent lamp as well as for the slide contact 8. In this instance, to facilitate the ready exchangeability of the retainer 7, the last-mentioned has an easily removable snapring-like securing element 7a associated therewith. Suitably, also the slide contacts 8 are arranged so as to be exchangeable on the retainer 7 and/or the contact rings 9 on the drive component 1. For this purpose, for instance pursuant to FIG. 7, the contact rings 9 are connected by means of plug connectors 9a with the power supply lines 10 which are arranged in the connector portion 1. The slide contacts 8 can be arranged in similar manner.

The engaging means 12 of the retainer structure consists of a detent which extends axially in its recessed extension, and the complementary or cooperating engaging means 11 on the gripping sleeve portion 2 consists of a similarly axially extending protuberance.

The retainer 7 is arranged on a rotatable turn ring 14 which is rotatably located on a trunnion-shaped or stub shaft-like extension 13 of the connector portion 1. The trunnion-shaped extension is insertable into the end of the gripping sleeve portion 2 which is distant from the implement, and as a result the gripping sleeve portion 2 is rotatable about the extension 13 which, suitably, evidences a circular cross-section.

Figure 6:
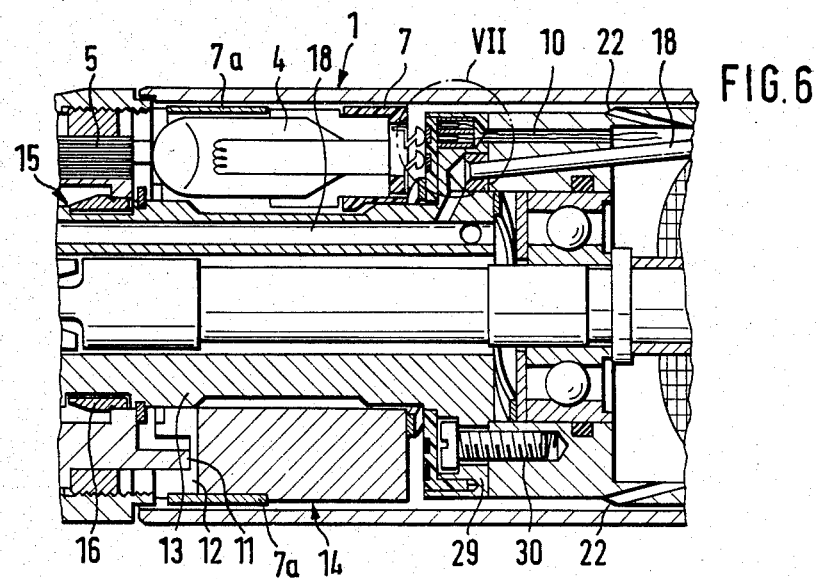
FIG. 6 is a view of a modified embodiment of the invention relative to that shown in FIG. 3.

In the embodiment pursuant to FIGS. 3 and 6 of the drawings, there is provided a locking arrangement which retains the extension 13 in the desired inserted position, which consists of a coupling ring 16 resiliently-yieldable in the radial direction, which encompasses the extension 13, and which in the coupled condition thereof is also freely rotatable and axially secured. In the coupled condition, representing the desired inserted position, the coupling ring will load-transmissively and radially resiliently contact against the inner wall of the gripping sleeve portion 2 in such a manner, such that the coupled together portions 1, 2 can be released from the other through axial pulling apart upon overcoming the clamping force of the coupling ring 16.

In the desired inserted position, the engaging means 12 are in engagement with the complementary or cooperating engaging means 11, so that the slide contacts 8 are in touching relationship with the contact rings 9 whereby the incandescent lamp 4 will burn and the end 5a of the light conductor 5, which is distant from the connector portion will emit light.

The gripping sleeve portion 2 additionally contains at least one supply medium conduit 17; for example, for a cooling medium, which is connectable through a connector conduit 18 in the connector portion 2 to a medium source (not shown) by means of a supply conduit (not shown) which is arranged exteriorly of the handpiece. For this purpose, the gripping sleeve portion 2 and the connector portion 1 are provided with medium transfer means operative in every position of rotation which, pursuant to FIG. 3, are formed through a discharge opening 20 of the connecting conduits 18 presently arranged between two seal elements 19 encompassing the extension 13, and which come into contact with the inner wall of the gripping sleeve portion 2; and through an annular passageway 21 associated with the discharge opening 20 and provided in the region of the inner wall of the gripping sleeve portion 2, which is in communication with the supply medium conduit 17. Pursuant to FIGS. 3 and 6, the connecting conduit 18 which conveys the cooling medium; for instance, air, water or a spray consisting of an air-water mixture, includes a branch line 22 leading to the incandescent lamp 4 for the purpose of cooling the latter.

Figure 7:
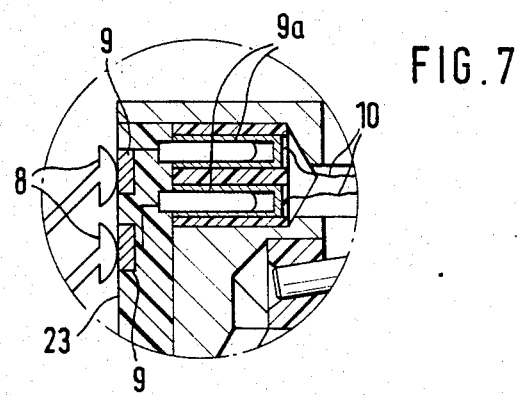
FIG. 7 illustrates, on an enlarged scale, the encircled section VII in FIG. 6.

In the embodiment according to FIG. 7, the annular contacting surface of the contact rings 9 which stand in contact with the slide contacts 8 is arranged on a circumferential surface of the connecting portion 1 which is located in a radial plane 23. In contrast therewith, in the embodiment pursuant to FIG. 3, the annular contacting surface of the contact rings 9 which stands in contact with the slide contacts 8 is arranged on a circumferential surface of the connector portion 1 which lies within a cylindrical shell ring 24.

Figure 2:
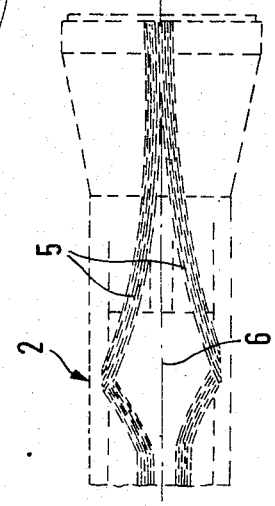
FIG. 2 illustrates a plan view of a portion of the gripping sleeve portion of the handpiece of FIG. 1, shown turned through an angle of 90°.

As can be ascertained in particular from FIG. 1, arranged interiorly of the gripping sleeve portion 2, and adapted to be coupled with drive means 25, for example, formed by a drive motor, located interiorly of the connector portion 1, are, drive transmission means 26, for instance formed by a shaft, for the drive of the, for example rotatable treating implement 3, wherein the light conductor 5 which, pursuant to FIG. 2, can also be formed of two wires, extends besides the drive transmission means 26.

The connector portion 1 possesses an outer sleeve 27 which radially covers the lightbulbs or incandescent lamp and, consequently, also the retainer 7, which has its end facing towards the gripping sleeve portion, in the coupled condition of the connector portion 1 and the gripping sleeve portion 2, contacting the end of the gripping sleeve portion which is remote from the implement and, in the uncoupled condition of the connector portion 1 and the gripping sleeve portion 2, upon overcoming the clamping force of a locking device 28 determining its desired inserted position, can be withdrawn from the connector portion in the direction of the end facing the gripping sleeve portion.

The stub shaft trunnion-shaped extension 13 possesses at its end which is distant from the gripping sleeve, an annular flange 29 which contacts against the end wall surface of the connector portion 1 facing towards the gripping sleeve portion, and which can be fixedly fastened to the referred to end wall surface by means of three screws 30. According to FIG. 3, a cooling medium branch conduit 22 leading to the incandescent lamp 4 is axially conducted through at least one of the screws 30.

What is claimed is:

1. In a dental handpiece, including a connector portion and an elongated, removable gripping sleeve portion coupled to the connector portion so as to be axially rotatable thereabout; a treating implement arranged on a forward end of said sleeve portion distant from the connector portion; incandescent lamp means arranged eccentrically in said handpiece; and light conductor means in said gripping sleeve portion and having a forward end remote from the connector portion directed towards the treating implement, and a rearward end adapted to receive light from said incandescent lamp means; the improvement comprising in that said incandescent lamp is rotatable in conjunction with the gripping sleeve portion relative to the connector portion; slide contacts cooperate with contact rings to connect said incandescent lamp means with power supply lines in said connector portion; said incandescent lamp is arranged on a retainer rotatable along an arcuate path about a longitudinal axis of the handpiece; the retainer is arranged on a forward end of the connector portion facing the gripping sleeve portion; and said retainer includes first engaging means cooperating with complementary second engaging means on the gripping sleeve portion upon alignment of the incandescent lamp means with the rearward end of the light conductor means for transmission of the rotational movement of said gripping sleeve portion.

2. Handpiece as claimed in claim 1 wherein said retainer the slide contracts and said incandescent lamp means are releasably held on said handpiece.

3. Handpiece as claimed in claim 2, further including a readily releasable securing element holding the retainer on said handpiece.

4. Handpiece as claimed in claim 1 wherein the slide contacts are releasably held on the retainer and the contact rings are releasably held on the connector portion.

5. Handpiece as claimed in claim 4, wherein said contact rings include plug connectors communicating with power supply lines in the connector portion to facilitate release of said contact rings.

6. Handpiece as claimed in claim 1 wherein the first engaging means comprisies an axially extending detent, and the complementary second engaging means comprises an axially extending protuberance.

7. Handpiece as claimed in claim 1 wherein said connector portion includes a trunnion-shaped extension, and said retainer is arranged on a swivel ring rotatably mounted on said extension.

8. Handpiece as claimed in claim 7, wherein said extension is insertable into the gripping sleeve portion and the gripping sleeve portion is rotatable about said extension.

9. Handpiece as claimed in claim 8, further comprising latching means for locking said extension into the gripping sleeve in a position with the first engaging means in operative engagement with the complementary second engaging means and the slide contacts in contact with the contact rings.

10. Handpiece as claimed in claim 9, wherein said latching means comprises a radially resilient coupling ring encompassing and clamped on said extension, said ring being freely rotatable and axially secured and load-transmissively contacting the inner wall of the gripping sleeve portion whereby the gripping sleeve portion and the coupling portion are disconnected from each other by pulling the gripping sleeve portion and the coupling portion axially apart and overcoming the clamping force of said coupling ring.

11. Handpiece as claimed in claim 1 wherein the contact rings include annularly extending contacting surfaces on a radial plane of the connector portion and in contact with the slide contacts.

12. Handpiece as claimed in claim 1 wherein the contact rings include annularly extending contacting surfaces of the connector portion held within a cylindrical shell ring.

13. Handpiece as claimed in claim 1 wherein the connector portion includes drive means, the gripping sleeve portion included transmission means to transmit motion from the drive means to the treating implement, and said light conductor means extends adjacent the transmission means.

14. Handpiece as claimed in claim 1 wherein the forward end of the connector portion includes an outer sleeve forming a radial covering for the incandescent lamp means.

15. Handpiece as claimed in claim 14 further including latching means releasably holding the outer sleeve in an assembled position.

16. Handpiece as claimed in claim 15 wherein the outer sleeve is disconnected from the connector portion by moving the outer sleeve axially forward.

17. Handpiece as claimed in claim 14 wherein a forward end of the outer sleeve is closely adjacent a rearward end of the gripping sleeve portion.

18. Handpiece as claimed in claim 14 wherein the outer sleeve is releasably connected to the connector portion.

19. In a dental handpiece, including a connector portion and an elongated removable gripping sleeve portion coupled to the connector portion so as to be axially rotatable thereabout; a treating implement arranged on a forward end of said sleeve portion distant from the connector portion; incandescent lamp means arranged eccentrically in said handpiece; and light conductor means in said gripping sleeve portion and having a forward end remote from the connector portion directed towards the treating implement, and a rearward end adapted to receive light from said incandescent lap means; the improvement comprising in that said incandescent lamp means is rotatable in conjunction with the gripping sleeve portion relative to the connector portion; slide contacts cooperate with contact rings to connect said incandescent lamp means with power supply lines in said connector portion; the gripping sleeve portion includes at least one supply medium conduit, the connector portion includes a connector conduit having a discharge opening located between two sealing elements extending around the connecting portion and contacting an inner wall of said gripping sleeve portion; and the gripping sleeve and the connector portion form an annular passageway forward of the incandescent lamp means and in communication with the discharge opening and the supply medium conduit of the gripping sleeve portion for conducting a fluid medium fron the connector portion to said supply medium conduit independent of the rotational positions of the connector portion and the gripping sleeve portion.

20. In a dental handpiece, including a connector portion and an elongated, removable gripping sleeve portion coupled to the connector portion so as to be axailly rotatable thereabout; a treating implement arranged on an end of said sleeve portion distant from the connector portion; incandescent lamp means arranged eccentrically in said handpiece; and light conductor means in said gripping sleeve portion and having a forward end remote from the connector portion directed towards the treating implement, and a rearward end adapted to receive light from said incandescent lamp means; the improvement comprising in that said incandescent lamp is rotatable in conjunction with the gripping sleeve portion relative to the connector portion; slide contacts cooperate with contact rings to connect said incandescent lamp means with power supply lines in said connector portion; the gripping sleeve portion includes at least one supply medium conduit, the connector portion includes a connector conduit in communication with the supply medium conduit for conducting a cooling fluid from a source thereof to the supply medium conduit, and the connector portion includes a branch conduit communicating with the incandescent lamp means for cooling said lamp means.

21. A gripping sleeve component for a dental handpiece having a drive component, the gripping sleeve component including an implement, an incandescent lamp, and a light conductor having a forward end directed to the implement and a rearward end adapted to receive light from said incandescent lamp, the improvement comprising:

the incandescent lamp is arranged on a rotatable retainer for rotating the lamp along an arcuate path in conjunction with the gripping sleeve component relative to the drive component;

a forward end of the retainer includes first engaging means cooperating with complementary second engaging means in the gripping sleeve component for transmitting rotational movement of the gripping sleeve component to the retainer after alignment of the incandescent lamp and the rearward end of the light conductor; and the gripping sleeve component includes transmission means for transmitting movement from the drive component to the implement, a medium supply conduit, and medium transfer means for conducting a fluid from the drive component to the medium supply conduit independent of the relative rotational positions of the gripping sleeve and drive components.

* * * * *